US011666693B2

(12) United States Patent
Mitschulat et al.

(10) Patent No.: US 11,666,693 B2
(45) Date of Patent: Jun. 6, 2023

(54) AUTOMATED METHOD FOR LEUKOCYTE COLLECTION FROM WHOLE BLOOD

(71) Applicant: Fresenius Kabi Deutschland, Bad Homburg (DE)

(72) Inventors: Heike Mitschulat, Wölfersheim (DE); Michael Brinkmann, Niddatal (DE)

(73) Assignee: Fresenius Kabi Deutschland, Bad Homburg (DE)

( * ) Notice: Subject to any disclaimer, the term of this patent is extended or adjusted under 35 U.S.C. 154(b) by 1048 days.

(21) Appl. No.: 16/324,178

(22) PCT Filed: Aug. 17, 2017

(86) PCT No.: PCT/EP2017/070824
§ 371 (c)(1),
(2) Date: Feb. 8, 2019

(87) PCT Pub. No.: WO2018/046268
PCT Pub. Date: Mar. 15, 2018

(65) Prior Publication Data
US 2019/0167889 A1 Jun. 6, 2019

(30) Foreign Application Priority Data
Sep. 6, 2016 (EP) .................................... 16187458

(51) Int. Cl.
*A61M 1/36* (2006.01)
*A61M 1/38* (2006.01)
(Continued)

(52) U.S. Cl.
CPC ........ *A61M 1/3696* (2014.02); *A61M 1/0209* (2013.01); *A61M 1/0272* (2013.01);
(Continued)

(58) Field of Classification Search
CPC .............. A61M 1/3696; A61M 1/0209; A61M 1/0272; A61M 1/382; A61M 2205/3303;
(Continued)

(56) References Cited

U.S. PATENT DOCUMENTS 5,102,407 A * 4/1992 Carmen .............. A61M 1/0209
210/411
5,383,847 A * 1/1995 Edelson ................. A61K 35/15
604/6.03
(Continued)

FOREIGN PATENT DOCUMENTS

CN 101312694 A 11/2008
CN 204234219 U 4/2015
(Continued)

OTHER PUBLICATIONS

D1: Claudia Del Fante et al "Clinical Impact of a new automated System employed for peripheral blood stem cell collection".
(Continued)

*Primary Examiner* — Shuyi S. Liu
(74) *Attorney, Agent, or Firm* — Cook Alex Ltd.

(57) ABSTRACT

The present invention relates to a method for separating lymphocytes and/or stem cells from whole blood in an automated blood separation system, wherein the quality of the collected lymphocytes and/or stem cells fractions is increased and the cell collection procedure is further automated by use of an optical sensor comprised in a detector device to measure turbidity and colour in the claimed method and in a cell separator, which can be used to perform the claimed method. The method of the invention is particularly useful to collect lymphocytes and/or stem cells fractions from whole blood, wherein the contamination of the collected cell fractions by platelets, red blood cells and granulocytes is reduced.

20 Claims, 7 Drawing Sheets

(51) Int. Cl.
*A61M 1/02* (2006.01)
*B04B 5/04* (2006.01)
*B04B 11/02* (2006.01)
*B04B 13/00* (2006.01)

(52) U.S. Cl.
CPC ........... *A61M 1/382* (2013.01); *B04B 5/0442* (2013.01); *B04B 11/02* (2013.01); *A61M 2202/0407* (2013.01); *A61M 2202/0437* (2013.01); *A61M 2202/0439* (2013.01); *A61M 2205/331* (2013.01); *A61M 2205/3303* (2013.01); *A61M 2205/3331* (2013.01); *B04B 2013/006* (2013.01)

(58) Field of Classification Search
CPC .. A61M 2205/3331; A61M 2202/0407; A61M 2202/0437; A61M 2202/0439; A61M 2205/331; B04B 5/0442; B04B 11/02; B04B 2013/006
USPC .............................................. 494/1, 2, 3, 10
See application file for complete search history.

(56) References Cited

U.S. PATENT DOCUMENTS

| | | | | |
|---|---|---|---|---|
| 5,607,579 A | * | 3/1997 | Latham, Jr. ......... | A61M 1/3696 210/195.1 |
| 5,936,714 A | * | 8/1999 | Gibbs ................. | G01N 21/532 356/39 |
| 6,752,777 B1 | * | 6/2004 | Takagi ................ | A61M 1/3672 210/782 |
| 2002/0020680 A1 | * | 2/2002 | Jorgensen ............ | B04B 5/0421 494/44 |
| 2004/0112808 A1 | * | 6/2004 | Takagi ................ | A61M 1/0218 210/143 |
| 2009/0166297 A1 | * | 7/2009 | Sweat ................. | A61M 1/3693 210/745 |
| 2010/0210989 A1 | * | 8/2010 | Macpherson ........... | B04B 11/02 604/6.03 |
| 2014/0039373 A1 | * | 2/2014 | Ragusa ............... | A61M 1/3693 604/5.01 |
| 2015/0043050 A1 | * | 2/2015 | Whitehead ........... | G02F 1/1347 359/238 |
| 2016/0114339 A1 | * | 4/2016 | Nguyen ................. | B04B 11/04 494/2 |

FOREIGN PATENT DOCUMENTS

| | | |
|---|---|---|
| EP | 2 896 418 A1 | 7/2015 |
| EP | 3 015 125 A1 | 5/2016 |
| WO | WO 94/25086 | 11/1994 |
| WO | WO 98/20345 A1 | 5/1998 |
| WO | WO 03/077013 A2 | 9/2003 |
| WO | WO 03/090839 A1 | 11/2003 |
| WO | WO 2009/085350 A1 | 7/2009 |

OTHER PUBLICATIONS

D2: Erwin F. Strasser: "Automated CD+14 monocyte collection with the autoMNC program of the COM.TEC cell separator".
International Search Report and Written Opinion for PCT Patent Application No. PCT/EP2017/070824, dated Nov. 22, 2017.

* cited by examiner

AUTOMATED METHOD FOR LEUKOCYTE COLLECTION FROM WHOLE BLOOD

RELATED APPLICATIONS

This application is a U.S. national stage application of PCT Patent Application Serial No. PCT/EP2017/070824, filed Aug. 17, 2017, which claims priority to European Patent Application Serial No. 16187458.1, filed Sep. 6, 2016, the contents of which are hereby incorporated by reference herein.

FIELD OF THE INVENTION

The present invention relates to a method for separating stem cells and/or lymphocytes from whole blood in an automated blood separation system, wherein the quality of the collected product is increased and the cell collection procedure is further automated by using a detector, which comprises an optical sensor to measure the colour and the turbidity in the fluid streams in the claimed method and in a cell separation system, which can be used to perform the claimed method.

BACKGROUND OF THE INVENTION

The present invention relates to the field of blood apheresis. Apheresis is any procedure in which blood is withdrawn from a donor/patient and a portion (such as plasma, leukocytes, platelets, or erythrocytes) is separated and retained, and the remainder is reinfused into the donor/patient. Types of apheresis include erythrocyteapheresis, leukapheresis, lymphocyteapheresis, stem cell apheresis, plasmapheresis, and plateletapheresis (thrombocyteapheresis).

Apheresis is also used in therapy, wherein whole blood is separated into its major components plasma and erythrocytes, and abnormal, pathogenic components are removed with the plasma in a therapeutic plasma exchange procedure; or abnormal erythrocytes are removed and exchanged by healthy cells in a red cell exchange procedure. Additionally to plasma exchange and red cell exchange (therapeutic procedures exist to remove white blood cells (leukapheresis), or platelets (thrombocyteapheresis).

Lymphocyteapheresis and stem cell collections are separation procedures to collect the mononucleated cell fraction containing lymphocytes and/or stem cells (flushed out from the bone marrow into the peripheral blood by a special medication) from withdrawn blood of a donor/patient, with the remainder of the blood reinfused into the donor/patient.

Blood apheresis is routinely performed using blood cell separators. Such blood cell separators usually comprise a centrifuge unit that is used to separate the blood components by density and size. Centrifugation methods can be divided into two basic categories: continuous flow centrifugation (CFC) and intermittent flow centrifugation. "Continuous" in the CFC method means that the blood is collected, spun, and returned simultaneously. The main advantage of this method and system is the low extracorporeal volume of the procedure. This is advantageous in particular, when small people, children, or patients with cardiac and circulatory troubles have to undergo an apheresis procedure.

Intermittent flow centrifugation works in cycles comprising the steps of taking blood, spinning, processing it, collecting one or more components, and returning the remainder components of the blood to the donor/patient in a bolus. In order to prevent blood from coagulation, anticoagulant agents are automatically mixed with the blood, when the blood is pumped from the body into the apheresis machine.

The end product of the blood centrifugation are sedimented erythrocytes at the outside of the separation chamber, the buffy-coat containing MNCs (MNC mononucleated cells, i.e. lymphocytes and monocytes,) stem cells, and platelets in the middle and the blood plasma at the inside of the separation chamber.

In recent years, automated apheresis systems have been developed. Automated clamps and sensors have been implemented in the devices. Furthermore, cell separators with centrifuge chambers that are particularly adapted to an automated separation of blood components have been developed.

EP 0985453 discloses a respective centrifuge chamber for a cell separator, especially for separating whole blood in its components.

EP 1025872 relates to a tube set for a cell separator for separating blood into its components and to a cell separator using said tube set. EP 1025872 further relates to a method for blood separation.

A known and commercially used cell separator is the COM.TEC® cell separator (Fresenius). The COM.TEC® device uses continuous flow centrifugation in order to separate blood components. Blood components are collected outside the centrifuge. Moreover, COM.TEC® uses sealless disposable sets. Only a low extracorporeal volume is necessary to operate the COM.TEC® device. Donation as well as therapeutic protocols can be run with the COM.TEC® device.

For therapeutic applications, for example for consecutive photochemotherapy or donor lymphocyte infusions (DLI), it is desired to collect lymphocytes with high purity from whole blood. The purity of the stem cell products is important with respect to the freezing and thawing process.

Together with monocytes the lymphocytes belong to mononuclear cells (MNCs). In a preferred embodiment of the invention, it is especially desired to separate MNCs containing the lymphocytes and/or stem cells in the buffy-coat fraction from whole blood.

It is in general possible to separate the buffy-coat, which contains the MNCs with the target cells (lymphocytes and/or stem cells) from whole blood by centrifugation using the COM.TEC® apheresis system.

For automated collection of MNCs, the COM.TEC® system contains a detector device that contains an optical sensor which detects that cells pass the sensor and triggers a processor device to initiate the collection of the target cells (lymphocytes and/or stem cells) comprised in the buffy-coat.

However, the existing conventional system has a disadvantage: the buffy-coat volume can be very small and the collected target cell fractions may be contaminated with too many red blood cells. This is, because the collection of the target cells is conventionally performed on the basis of predefined volumes, but is not automatically stopped when the content of red blood cells increases in the buffy-coat stream during the collection of the target cells.

DESCRIPTION OF THE INVENTION

Accordingly, it is the purpose of the present invention to improve the automated collection procedure of the target cells (lymphocytes and stem cells), which are comprised in the buffy-coat, from whole blood and thereby, to overcome the disadvantage of the prior art.

This problem is solved by a method comprising the steps according to claim 1.

Specifically, the method for separating lymphocytes and/or stem cells from whole blood according to the invention is performed in an automated blood cell separation device.

The automated blood cell separation device according to the invention is suitably a continuous flow separator working with intermittent collection cycles in the context of a new, fully automatic collection system, called autoMNC, with sub-procedures to collect stem cells and/or lymphocytes. The patient's/donor's characteristics (weight, height, and sex), and cell pre-counts (concentrations of WBC, CD34+ cells) and Hct %) are entered into the menu of the cell separator. Based on these values, the device calculates the optimal collection parameters (cycle volume, buffy-coat volume, processed blood volume). The adaptation of the yield desired can be done by a modification of the number of cycles.

Each cycle consists of 3 automatic phases:
1. During the separation phase, whole blood is separated in the separation chamber into a red blood cell layer, a MNC (mononuclear cells) layer, called buffy-coat, and platelet-rich plasma (PRP). While the red blood cells and PRP are returned directly back to the patient/donor, the MNC layer is accumulated within the separation chamber in a defined position controlled by an optical camera system. The mature granulocytes are within the red blood cell layer
2. After reaching the cycle volume, the spillover phase starts: the MNC layer is pumped via the plasma exit out of the separation chamber up to an optical sensor that controls a collection clamp.
3. When this sensor detects cells, it automatically stops the spillover phase and immediately starts the buffy-coat phase: the sensor closes the path back to the patient and opens the path up to the collection container.

The automated blood cell separation device according to the invention comprises generally a front panel with a graphic user interface (GIU), pumps, automatic clamps and detector devices comprising optical sensors for monitoring fluid streams, an iv pole for attaching the saline and anti-coagulant bags, prime bag, and the collection containers for target cells and plasma. The automated blood cell separation device further comprises a centrifuge compartment, which comprises a rotor with a mechanism to install a chamber holder for holding the separation chamber for the automated separation of blood fractions from whole blood. The separation chamber and the containers are connected to each other by a tubing system. The pumps are preferably peristaltic pumps and transport the blood, blood fractions, and solutions between the aforementioned parts of the automated blood cell separation device. The automatic clamps are controlled by a processor device of the automated blood cell separation device and assist to direct the fluid stream in the tubing system to the desired part of the tubing system installed on the automated blood cell separation device.

After the blood is supplied to the tubing set installed on the automated blood separation system, the red blood cell and plasma fractions are separated in a separation chamber of a centrifugation unit. During this step, the saline solution is diverted from the separation chamber and an outer layer, which comprises the red blood cells, and an inner layer, which comprises the blood plasma, are formed. The buffy-coat is accumulated as a further layer between the red blood cell and plasma fractions in the separation chamber. Thereafter, in a so-called condensation phase the buffy-coat is positioned exactly in the separation chamber, before the spillover is started.

The position of the buffy-coat layer between the outer red blood cells layer and the inner plasma layer in the separation chamber of the automated blood cell separation device is suitably monitored by a monitoring device comprising an 8 hole imprint on the separation chamber, and an optical sensor, which is suitably a camera system.

During the spillover phase special flow rates of blood going into the separation chamber and the plasma going out of the chamber cause a negative pressure within the separation chamber supporting the removal of the buffy-coat from the chamber and pump it into the plasma line. During the subsequently following buffy-coat phase, the buffy-coat and plasma fractions are spilled over to the front panel of the automated blood cell separation device and the target cells (lymphocytes and/or stem cells), are pumped into the collection container.

Accordingly, the method for separating lymphocytes and/or stem cells from whole blood according to the invention comprises generally the steps of
supplying blood to the tubing set installed on the automated blood cell separation device,
separating the red blood cell and plasma fractions in a separation chamber in a centrifugation unit, and accumulating the buffy-coat between the red blood cell and plasma fractions in the separation chamber;
condensation of the buffy-coat fraction in the separation chamber,
spillover of the buffy-coat and plasma fractions to the sensor at the front panel of the automated blood cell separation device,
transferring and collecting the lymphocytes and/or stem cells into a collection container.

In a further embodiment, the method for separating lymphocytes and/or stem cells from whole blood according to invention may comprise the step of
priming the tubing set installed on the automated blood cell separation device with a saline solution and an anti-coagulant solution.

Suitably, this priming step is performed as the first step before supplying blood to the tubing set. The tubing set is preferably primed with saline solution and anti-coagulant solution in order to drain any air from the blood separation system and in order to prevent the blood, which is to be separated into its fractions, from coagulation and from air contact.

It is the advantage of the method of the invention that lymphocytes and/or stem cells can be collected in an automated manner with reduced contamination of the collected product(s) by red blood cells. To prevent contamination of the lymphocyte and/or stem cells fractions that are collected with the automated method of the invention, at least two criteria are applied for transferring and collecting the target cells into a collection container. As a first criterion, the turbidity of the fluid stream is monitored in the tubing, which connects the separation chamber with the collection containers for collecting the buffy-coat. After initiation of the spillover, the buffy-coat, which comprises the target cells, is first transferred from the separation chamber to the sensor at the front panel of the automated blood cell separation device, followed by the red blood cell fraction. This sensor is part of the detection device according to invention; it is the so called spillover detector at the COM.TEC® device.

In a preferred embodiment of the invention, the transfer of the target cells into the collection container is initiated when the turbidity of the fluid stream, i.e. of the plasma fraction, increases. This increase in the turbidity of the plasma stream indicates that besides the platelets the target cells, (lymphocytes and/or stem cells) are contained in the fluid stream. The target cells are then transferred into a collection container as long as such increased turbidity is recognised in the fluid stream.

It is further desired that fractions of target cells (lymphocytes and/or stem cells) are collected, which are not contaminated by platelets, i.e. which have a reduced platelet count or are substantially free of platelets. Target cell fractions with reduced platelet count can be collected, when, in addition to the turbidity, also the colour, preferably the white colour of the fluid stream is monitored in the tubing, which connects the separation chamber with the collection containers. The fluid stream first has a slightly yellowish colour. This yellowish colour of the fluid stream drops, when "white" buffy coat passes the sensor. White buffy coat indicates the presence of platelets in the monitored fluid stream. The end of the platelet fraction is indicated by a colour increase of the fluid stream, which now comprises the lymphocytes and/or stem cells, which have a reduced platelet count or are substantially free of platelets. Accordingly, the transfer and collection of lymphocytes and/or stem cells with reduced platelet count is started immediately upon the increase of the turbidity and the colour of the fluid stream after the white buffy coat has passed the spillover detector.

According to the invention, the transfer and collection of the target cells in a collection container is automatically stopped, when the colour, preferably the red colour of the fluid stream reaches a predefined threshold. Such increase in the red colour in the fluid stream indicates that now the red blood cell fraction is spilled-over from the separation chamber to the sensor at the front panel of the automated blood cell separation device.

Accordingly as a second criterion, the colour of the fluid stream, preferably the red colour in the fluid stream is monitored.

In a more preferred embodiment of method of the invention, there are thus at least two criteria applied for transferring and collecting the target cells into a collection container, wherein
- as a first criterion the turbidity of the fluid stream is monitored and the transfer of the target cells into the collection container is initiated when the turbidity of the fluid stream increases, and
- as a second criterion the colour of the fluid stream, preferably the red colour, in the fluid stream is monitored and the transfer of the target cells into the collection container is terminated, when a predefined threshold of the red colour is reached in the fluid stream.

In a most preferred embodiment of method of the invention, when target cell fractions with a reduced platelet count shall be collected, there are the following criteria applied for transferring and collecting the target cells into a collection container, wherein
- as a first criterion the turbidity and colour, preferably the white colour of the fluid stream is monitored and the transfer of the target cells into the collection container is initiated when the turbidity of the fluid stream increases and the colour of the fluid stream increases after the white buffy coat has passed the sensor, and
- as a second criterion the colour of the fluid stream, preferably the red colour, in the fluid stream is monitored and the transfer of the target cells into the collection container is terminated, when a predefined threshold of the red colour is reached in the fluid stream.

For monitoring of the turbidity and colour of the fluid stream during the spillover and the target cell collection phase, the automated blood cell separation device according to the invention comprises a detector device. This detector device comprises an optical sensor, which comprises a red transmit LED (light emitting diode) for turbidity measurement and a green transmit LED for measuring the absorption of the emitted green light by red blood cells in the plasma and/or the buffy-coat stream. In a preferred embodiment of the invention, both, the light transmitted through the fluid stream and the light emitted to the rear, are detected by photo transistors and the rearward measurement section serves as a reference measurement brunch to enable the compensation for aging effects and temperature drift in the transmit LEDs.

The red colour of the fluid stream corresponds to a hematocrit value. Accordingly, target cell collection is terminated, when a predefined threshold of the red colour is measured by the optical sensor comprised in the spillover detector in the fluid stream, wherein the red colour corresponds to a certain hematocrit value. More preferably, target cell collection is terminated, when the red colour in the fluid stream measured by the optical sensor comprised in the spillover detector reaches a threshold corresponding to a hematocrit value of up to 25%, preferably up to 20% or 15%, more preferably up to 14%, 13%, 12%, 11% or 10%, most preferably up to 9%, 8%, 7%, 6% or 5%.

Even most preferably, target cell collection may be terminated, when the hematocrit of the collected product in the collection container reaches a value of 10%, 9% or 8%, when stem cells are collected, and of 5%, 4%, 3% or 2%, when lymphocytes are collected.

The hematocrit (Hct) value is the volume percentage (vol %) of red blood cells in blood.

The collection of the target cells is not terminated, when the red colour measured in the fluid stream has a value, which corresponds to a hematocrit below the above defined percentages. Terminating the collection of the target cells, when the threshold of the red colour corresponding to a predefined hematocrit value is reached, ensures that the contamination of the collected target cell fractions with red blood cells can effectively be prevented.

The method of the present invention can be performed in several cycles. This ensures that a sufficient amount of target cells in the buffy-coat can be collected from a patient/donor.

Typically, there is a construction based distance between the spillover clamp and the spillover detector. The target cells between spillover clamp and spillover detector would be lost, when the spillover clamp closes the tube to the collection container immediately, after the optical sensor comprised in the spillover detector has measured a red colour that corresponds to the predefined threshold.

Therefore, in a further preferred embodiment, in order to avoid this loss of target cells, the target cell collection is terminated after detection of the red colour threshold by the optical sensor of the spillover detector and after collecting an additional defined volume of buffy-coat comprising the target cells. Suitably, such additionally collected volume of buffy-coat is in the range of 0 to 5 ml, preferably 0 to 4 ml, more preferably 0 to 3 ml, most preferably 0 to 2 ml or 1 to 2 ml.

When the method of the present invention is performed for several cycles, then the additional volume of buffy-coat, which comprises the target cells, is collected within the first five to ten cycles (about half of the total procedure) after detection of the red colour threshold by the spillover detector, but before termination of the collection of the target cells. In the second half of the procedure this volume is usually decreased, preferably by 50%, because during the first half of the procedure the volume of the buffy-coat usually decreases. This embodiment has the advantage that contaminations of the target cell fractions with, for example red blood cells, can effectively be prevented.

Accordingly, in a preferred embodiment of the invention, the target cell fraction that is collected with the method of the invention, substantially contains lymphocytes and/or stem cells. "Substantially contains lymphocytes" means that the cell count of granulocytes is in a low range, i.e. that the lymphocytes and/or stem cells collected with the method of the invention are substantially free of granulocytes. In a preferred embodiment of the invention, "substantially contains lymphocytes" means that the cell count of granulocytes and platelets is in a low range, i.e. that the lymphocytes and/or stem cells collected with the method of the invention have reduced counts of granulocytes and platelets or are substantially free of granulocytes and platelets.

Contamination of the collected target cell fractions with red blood cells can be estimated using the hematocrit value of the collected target cell fractions. DelFante et al., Journal of Clinical Apheresis 21:227-232 (2006), have investigated the COMTEC® device (Fresenius) deploying the conventional autoMNC procedure. Stem cell collections (i.e. collections of the buffy-coat), which were obtained with this method from patients and donors had hematocrit values of 10.9 and 9.2%, respectively. With the method of the present invention, it is possible to provide target cell collections, which have a hematocrit value below 10%, 9% or 8%, when stem cells are collected as the product, and below 5%, 4%, 3% or 2%, when lymphocytes are collected as the product.

In the operational mode, the automated blood cell separation device is directly connected to a donor/patient and the blood, which is to be separated, is obtained via a needle from the donor/patient vein and supplied directly to the automated blood cell separation device. Fractions of the separated blood, such as plasma and red blood cells in this operational mode, are reinfused to the donor/patient via a respective tubing via a second needle into the patient/donor vein (dual needle procedure with two different venous punction sites).

The automated blood separation device according to the invention may also be operated in an 'offline' mode. In this operational mode, the automated blood separation device is not connect to a patient. The blood separation is performed based on blood samples that were already collected from a patient before performing the blood separation method according to the invention. The blood samples are then provided in blood bags, which are connected to the automated blood separation device via a respective tubing. Likewise, unwanted blood fractions, such as plasma and red blood cells are not reinfused into the patient, but collected in a respective collection container.

In a further preferred embodiment the automated blood cell separation device according to the invention comprises a spillover detector that comprises an optical sensor which monitors the turbidity of the fluid stream in the tubing of the front panel after initiating the spillover in the separation chamber. Accordingly, by using the spillover detector, it is recognized, when the target cells are present in the plasma which is spilled-over from the separation chamber. Usually, the plasma fraction is, depending on the operational mode of the automated blood cell separation device, either reinfused into the patient or partially collected in a collection container as a by-product. The spillover detector triggers one of the automated clamps, namely the so-called plasma collection clamp to change its position and to redirect the fluid stream from "reinfusion" of the plasma into the position to "transfer and collect" the plasma into a plasma collection container.

In an especially preferred embodiment of the present invention, not only the turbidity in the fluid stream after initiating the spillover in the separation chamber is monitored by the optical sensor of the spillover detector, but additionally the colour, especially the red colour of the fluid stream is monitored by the same optical sensor.

The automated blood cell separation device further comprises a processor device, which receives the signals from the spillover detector and which triggers the spillover clamp to change its position.

Thus, in a further preferred embodiment of the method of the invention, the spillover detector triggers a signal to the processor device when the turbidity of the fluid stream, after initiating the spillover in the separation chamber, rises and when the colour of the fluid stream increases after the white buffy coat, which contains the platelets has passed the sensor comprised in the spillover detector; and the processor device triggers the initiation of the transfer and collection of the buffy-coat, which comprises the target cells (lymphocytes and/or stem cells) by opening the spillover clamp into the direction of the respective target cell collection container.

In an even preferred embodiment of the method of the invention, the spillover detector triggers again a signal to the processor device as soon as a predefined threshold of the red colour of the fluid stream, i.e. of the buffy-coat stream, is reached and the processor device triggers the termination of the transfer and collection of the target cells into the target cell collection container by changing the position of the spillover clamp, thereby reinfusing the subsequently spilled-over red blood cells into the donor/patient or transferring them into a respective collection container.

The method of the invention has several advantages. In particular, all disadvantages of the prior art methods and of the conventional automated cell separation systems can be optimized. In contrast to conventional methods, where the collection of the the target cells is stopped manually, i.e. by a user pressing the "STOP PHASE" button of the automated cell separation device, or after collecting a default volume of the buffy-coat, which comprises the target cells, the spillover detector now stops the buffy-coat phase automatically. The collected volume of the target cell fractions is depending on the hematocrit in the fluid stream. It is thereby ensured that the red blood cells are returned to the donor/patient before the buffy-coat concentrate tail at the beginning of the reinfusion is pushed into the target cell collection container. It can be further ensured that a maximum yield of target cells is collected.

With the method of the present invention, it is possible to collect target cells in an automated procedure with a higher quality than it is possible with conventional methods. In a further embodiment, the invention therefore relates to target cells obtainable by the method of the invention, preferably to lymphocytes, monocytes and/or stem cells obtainable with the method of the invention.

The target cells, in particular the lymphocytes and/or stem cells separated and collected with a method according to the invention can be used in therapy. Accordingly, the invention provides in further embodiments the use of the lymphocytes and/or stem cells collected with the method of the invention in therapy. The stem cells collected with a method of the invention are particularly useful for the treatment of certain cancers after photochemotherapy or high-doses chemotherapy, through which stem cells in the blood stream of a patient are damaged irreversibly. The lymphocytes collected with a method of the invention are particularly useful for donor lymphocyte infusions and/or for the treatment of skin diseases and graft versus host disease.

The object of the invention is also achieved by a blood cell separation device for separating lymphocytes and/or stem cells in the buffy-coat from whole blood in an automated procedure, comprising:
- a pumping section for pumping a fluid through a tubing set installed at the automated blood cell separation device,
- a centrifuge compartment, which comprises a separation chamber for the automated separation of buffy-coat from whole blood,
- a detector device comprising an optical sensor for measuring a measurement value indicative of the presence of cells in the plasma stream, and for measuring a measurement value indicative of the presence of red blood cells in the plasma/buffy-coat tube,
- an automatic clamp for directing the plasma stream into the direction "reinfusion" and for directing the buffy-coat stream into direction "collection" and
- a processor device for controlling the automatic clamp, the processor device being constituted to switch the position of the automatic clamp into the direction of "collection" in case of target cells, such as lymphocytes and/or stem cells, being detected by the detector device in the plasma/buffy-coat tube, and the processor device being further constituted to switch the position of the automatic clamp into the direction of "reinfusion" in case of red blood cells being detected by the detector device in the plasma/buffy-coat tube.

Herein, for transferring and collecting the buffy-coat into a collection container, at least two criteria are applied, wherein
- as a first criterion the turbidity of the fluid stream in the plasma/buffy-coat tube is monitored and the transfer of the target cells into the target cell collection container is initiated when the turbidity of the fluid stream in plasma/buffy-coat tube rises, and
- as a second criterion the colour of the buffy-coat stream, preferably the red colour, in the plasma/buffy-coat tube is monitored and the transfer of the target cells into the target cell collection container is terminated when a predefined threshold of the red colour of the fluid stream in the plasma/buffy-coat tube is reached.

When target cells fractions with a reduced platelet count shall be collected, then for transferring and collecting the buffy-coat into a collection container, the following criteria are applied, wherein
- as a first criterion the turbidity and colour, preferably the white colour of the fluid stream is monitored and the transfer of the target cells into the collection container is initiated when the turbidity of the fluid stream increases and the colour of the fluid stream increases after the white buffy coat has passed the sensor, and
- as a second criterion the colour of the buffy-coat stream, preferably the red colour, in the plasma/buffy-coat tube is monitored and the transfer of the target cells into the target cell collection container is terminated when a predefined threshold of the red colour of the fluid stream in the plasma/buffy-coat tube is reached.

The advantages and advantageous embodiments described above for the method equally apply to the blood cell separation device such that it shall be referred to the above.

The idea underlying the invention shall subsequently be described in more detail with regard to the embodiments shown in the figures. Herein.

Figure 1:
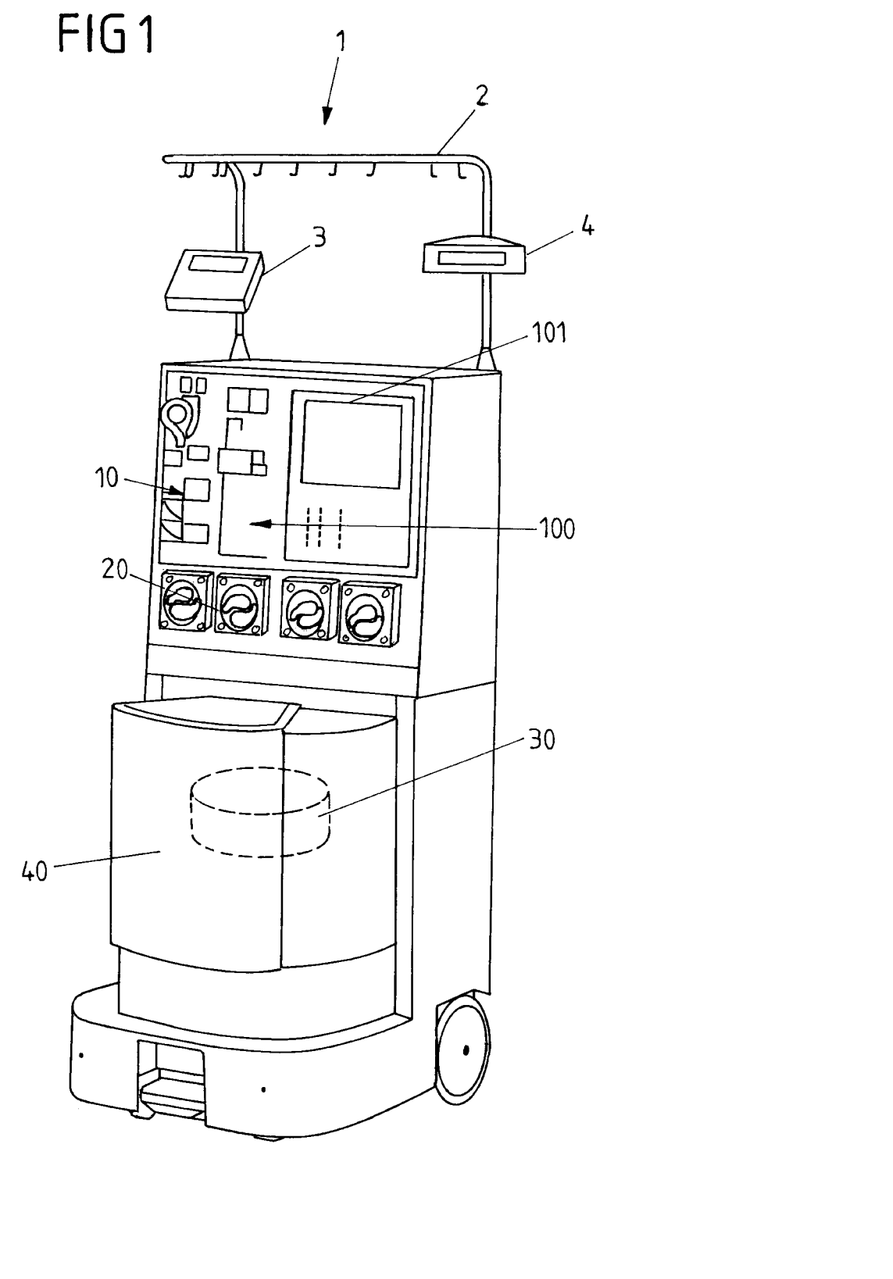
FIG. 1 shows a general overview on the automated cell separation device used in the method according to the invention.

FIG. 1 shows the general assembly of the automated blood cell separation device 1 comprising an IV pole 2, a printer 3, a donor display 4, wheels 5, automatic clamps 10, a pump section 20, a centrifuge compartment 40, and a front panel 100.

The IV pole 2 is constructed to attach collection and stock bags, such as the target cell collection container or, for example the saline and anti-coagulant stock bags.

The printer 3 permits the recording of the entire program sequence during the automated blood separation. Suitably, volumes and flow rates displayed during the program are printed out with clock time. That points for the separation are printed when starting the separation program and actual values are printed periodically during the program, for example every 1000 ml of whole blood.

The donor display 4 is suitably a two-line LED display which indicates information for the donor/patient, such as time, remaining treatment time and alarms.

The centrifugation compartment 40 comprises a centrifugation unit and the separation chamber for performing the method of the present invention.

Figure 2:
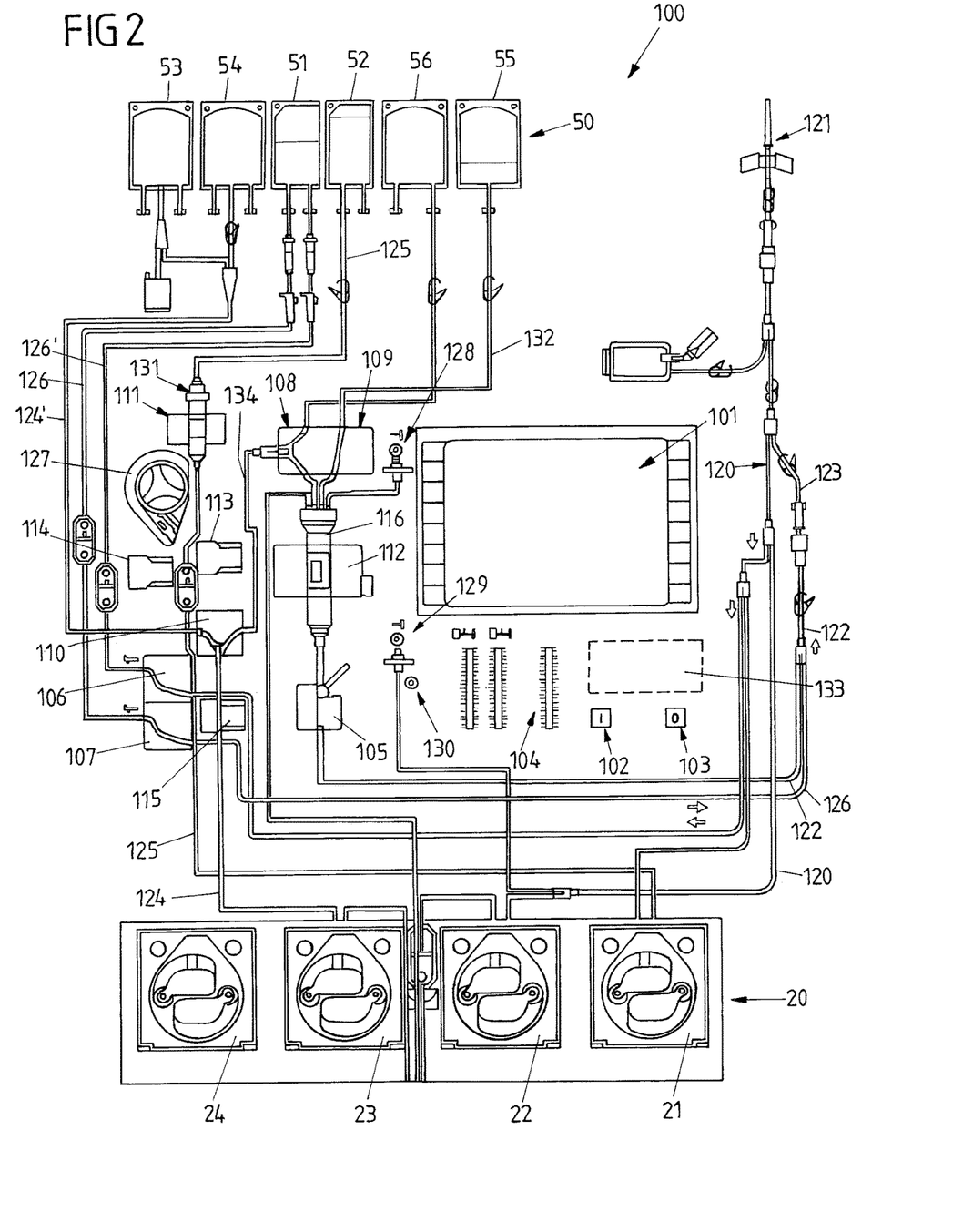
FIG. 2 shows a detailed view on the front panel of the automated cell separation device.

FIG. 2 shows a detailed view on the front panel 100 of the blood cell separation device 1. The front panel 100 further comprises a graphic user interface 101, which is suitably a colour LCD display. The section of blood pumps 20 comprises an ACD pump 21, a whole blood pump 22, which delivers the anti-coagulated whole blood to the centrifugation compartment 40, a plasma pump 23, which establishes and during the collection phase maintains the interface position (position of the buffy-coat layer) in the separation chamber together with the blood pump 22, and a cell pump 24.

The automated blood cell separation device can be switched on with pressing the on-button 102 and it can be switched off by pressing the off-button 103. Pressure in the inlet line, outlet line (and not in use in leukapheresis: absorber columns) are monitored via the pressure monitors 104. For controlling pressure in the outlet line, the front panel contains pressure measurement port 128 for measuring the return pressure, pressure measurement port 129 for measuring the inlet pressure (and a further pressure measurement port 130 for measuring the transmembrane pressure of the column). When performing the method according to the invention, the set installed on the automated blood cell separation device 1 is first primed with an anti-coagulant solution from stock bag 52 and with a saline solution from bag 51, wherein both solutions are transferred to the tubing set by operating the ACD pump 21, the whole blood pump 22 and the plasma pump 23 and wherein the anti-coagulant solution is provided to the device 1 via prime solution tube 125 and the saline is provided to the set via the saline tubes 126 and 126'. To ensure an air-free delivery of the anti-coagulant solution, the anti-coagulant solution is delivered through the ACD-drip chamber 131. After priming of the tubing set installed on the automated blood cell separation device 1, the tubing set may be connected via the needles 121 and 123 to (a peripheral venous catheter of) a donor/patient. Alternatively, (a) stock bag(s) with blood samples that were already obtained from a patient can be connected to the device 1 via blood tube 120 and any unwanted blood fractions may be collected in respective collection containers via tubes 122.

The blood is then supplied from the donor/patient to the set installed on the automated blood cell separation device 1 via blood tube 120. Using whole blood pump 22, the blood from the patient is pumped into the centrifugation compartment 40. The separation chamber, which is part of the centrifugation compartment 40, is in this stage filled with the prime solution. Pumping the blood from the patient into the separation chamber by whole blood pump 22 results in the diversion of the prime solution from the separation chamber into the prime bag 55 via diversion tube 132. In the separation chamber, the whole blood is separated in the red blood cell, buffy-coat and plasma fractions. When separate layers of these fractions are established in the separation chamber, the buffy-coat is spilled over to spillover sensor at the front panel 100 by speeding up the plasma pump 23, and reducing the whole blood flow rate. The buffy-coat is pumped through tube 124. The fluid stream passes the spillover detector 115 and the spillover clamp 110. The spillover detector 115 monitors the turbidity of the passing plasma stream in tube 124. The plasma passes spillover clamp 110, which is open in direction of "return", meaning that the plasma separated from the whole blood is retransferred together with the red cells to the patient via tube 134 and the return tube 122. To ensure that the plasma and red cells returned to the patient, are free of air, the components pass the drip chamber 116 of the air detector 112. When the optical sensor comprised in the spillover detector 115 detects an increase of the turbidity in the plasma stream in tube 124, it triggers a signal to a processor device 133, which triggers spillover clamp 110 to switch in direction of "collection". The increase of the turbidity of the plasma stream measured in tube 124 indicates that the target cell fraction, i.e. mononuclear cells including lymphocytes and/or stem cells, are now passing the spillover sensor 115. Switching spillover clamp 110 from "return" to "collect" leads to the collection of the lymphocytes and/or stem cells comprised in the buffy-coat in collection containers 53 and 54 via buffy-coat tube 124'. The lymphocytes and/or stem cells are collected as long as the colour in the buffy-coat stream in tube 124 does not reach a predefined threshold of the red colour, which is monitored also by the optical sensor comprised in the spillover detector 115. When the spillover detector 115 measures a red colour, which corresponds to the predefined threshold, it triggers a signal to the processor device 133, which in turn triggers spillover clamp 110 to switch back from "collection" to "return". Reaching the predefined threshold of the red colour in tube 124 means that the buffy-coat has now passed and that red blood cells are in tube 124. The collection of the lymphocytes and/or stem cells is thus stopped automatically without user intervention.

The spillover detector 115 accordingly measures both, the turbidity and colouring of the related medium in the plasma or buffy-coat tube 124 installed on the automated blood cell separation device 1. More specifically, the spillover detector 115 comprises an optical sensor with a red and a green transmit LED that are activated alternately. Both, the light transmitted through the medium in the tube and the light emitted to the rear, are detected by photo transistors. The rearward measurement section serves as a reference measurement branch to be able to compensate for aging effects of the tubes and temperature drift in the transmit LEDs. The signals from the photo transistors are converted by two AD converters and sent via an SPI bus to a microcontroller. The spillover detector 115 must be calibrated for the specific sensor due to the tolerances on the individual sensors. The calibration data measured are saved via the SPI bus in an EEPROM. The red LED is used for turbidity measurement and the green LED is used for measuring the colour of the fluid stream in tube 124, especially the absorption of the emitted green light by red blood cells is measured in tube 124.

The automated blood cell separation device 1 may further comprise saline inlet line clamp 106 and saline return line clamp 107, which control the supply of saline for priming and for keep-vein-open function in stop condition and for reinfusion. The plasma collection clamp 108 is an automatic clamp controlling an optional additional plasma collection into the collection container 56. Diversion clamp 109 is an automatic clamp for controlling the saline diversion. The return clamp 105 is a fail-safe magnetic clamp that separates the donor/patient circulation from the circulation of the automated blood cell separation device 1 in the event of an alarm. This clamp contains suitably an integrated sensor for monitoring the return line.

The ACD detector 111 functions as drip counter for monitoring the anti-coagulant flow. The Hb/Hct detector 113 detects any possible haemolysis in the device 1 as well as errors during separation causing haemoglobin to enter the separated plasma. The replacement fluid end detector 114 detects air in the replacement fluid line 125.

Figure 3:
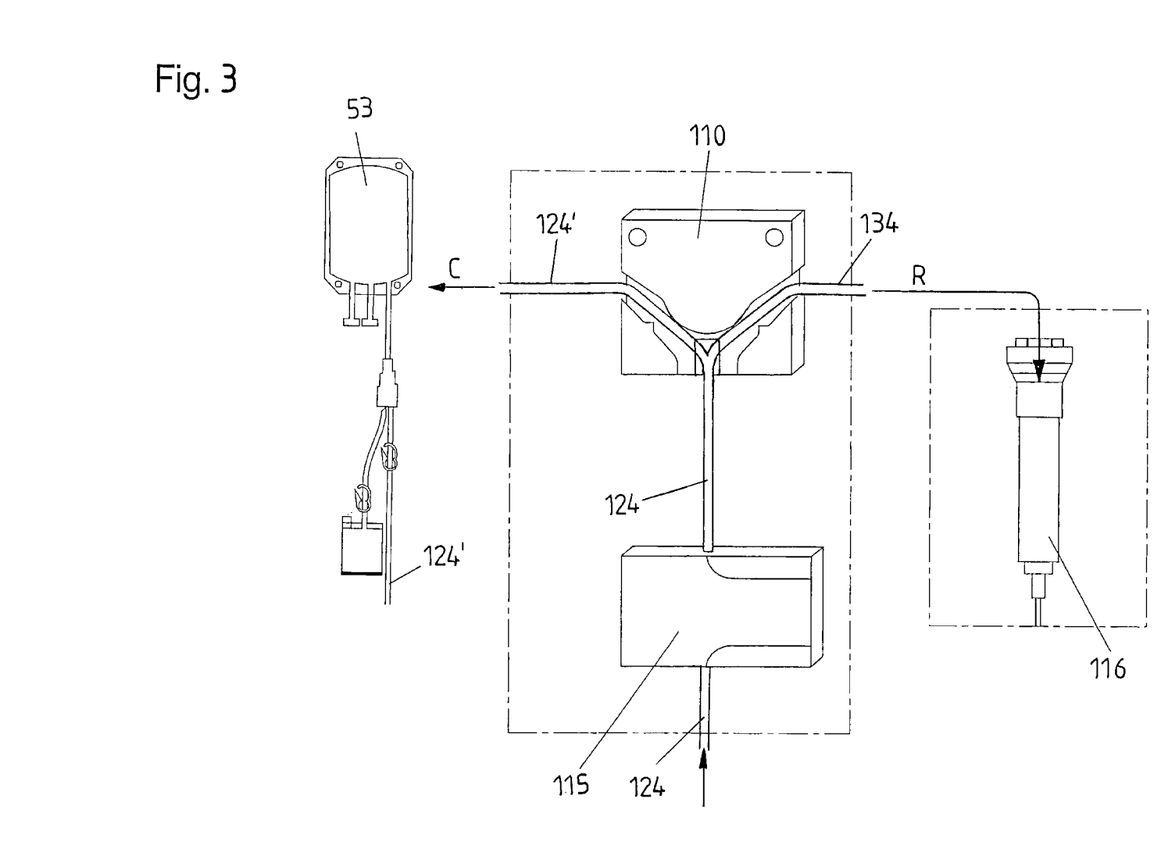
FIG. 3 shows the spillover detector and the spillover clamp as part of the automated cell separation device.

FIG. 3 shows the spillover detector 115 and the spillover clamp 110 of the automated blood cell separation device in more detail. The fluid stream (plasma or buffy-coat) is transported through the spillover detector 115 and the spillover clamp 110 via tube 124. The lower arrow indicated the flow direction F into the spillover detector. When the spillover clamp 110 is switched into the direction "return", then the plasma stream is reinfused into the patient as indicated by arrow R, thereby passing drip chamber 116 in order to prevent any air or air bubbles in the reinfused blood stream. When spillover clamp 110 is switched into the direction "collection" as indicated by arrow C, then the lymphocytes and/or stem cells comprised in the buffy-coat are transported via tube 124' into collection container 53 (see also FIG. 2).

As can be seen from FIG. 3, there is a construction based distance between the spillover clamp 110 and the spillover detector 115. The target cells between spillover detector 115 and spillover clamp 110 would be lost when the spillover clamp 110 closes the tube 124' to the collection container 53 immediately after the spillover detector 115 has measured a red colour corresponding to the predefined threshold.

In a preferred embodiment of the automated collection procedure according to the invention, the collection of lymphocytes and/or stem cells is terminated after detection of the predefined red colour threshold by the spillover detector 115 and after an additional default volume of buffy-coat, which comprises the target cells, is allowed to pass spillover clamp 110, in order to prevent the loss of the target cells. Suitably, this additional volume of buffy-coat is in the range of 0 to 5 ml, preferably 0 to 4 ml, more preferably 0 to 3 ml, most preferably 0 to 2 ml or 1 to 2 ml.

Figure 4:
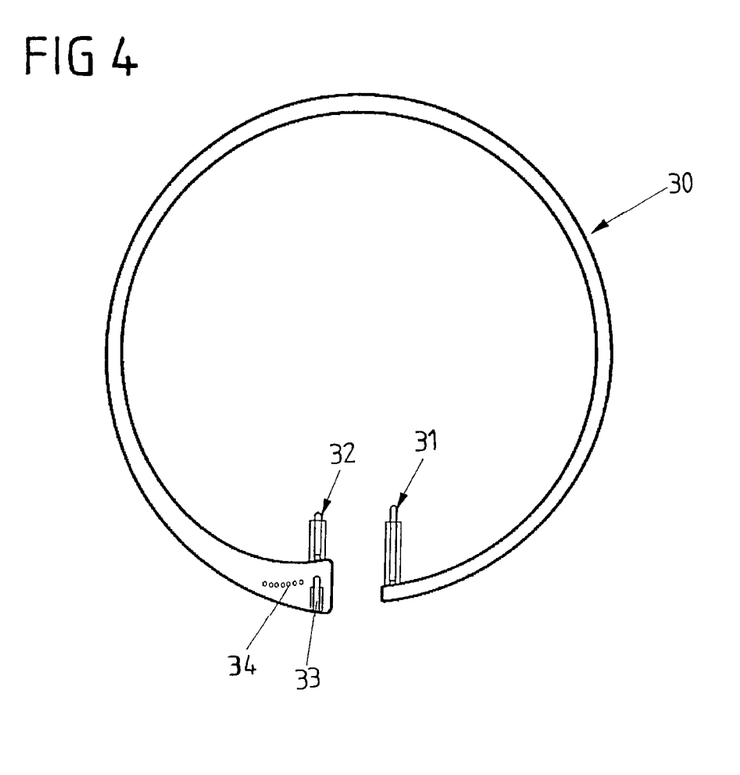
FIG. 4 shows the principal construction scheme of the separation chamber.

FIG. 4 shows a schematic representation of the separation chamber 30, which is empty. Separation chamber 30 comprises a blood port 31, an inner plasma port 32 and an outer erythrocyte port 33. The separation chamber 30 further comprises an imprint with 8 holes 34 for the monitoring of the interface position. Preferably, these monitoring windows 34 are arranged in an ascending series. Most preferably, separation unit 30 comprises eight monitoring holes, arranged in an ascending series.

Figure 5:
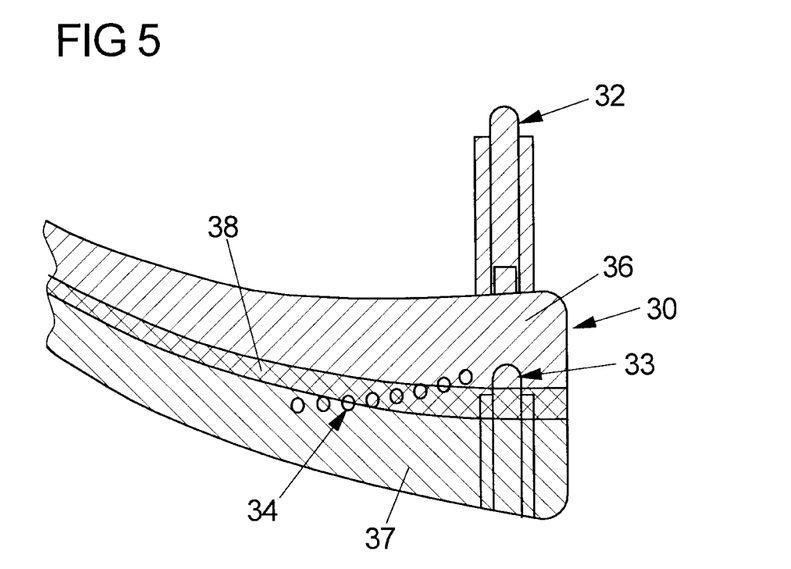
FIG. 5-FIG. 6 show phases of the automated blood separation in the separation chamber.
Figure 6:
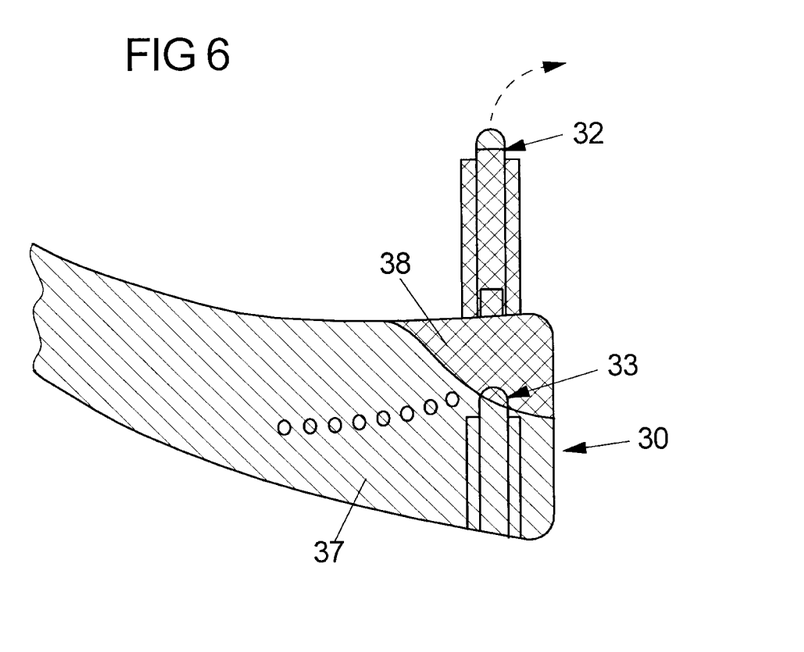

FIG. 5 and FIG. 6 show different stages of the separation process of whole blood in the filled separation chamber 30. When whole blood is pumped into the centrifugation unit 40, in particular into the separation chamber 30 through the blood port 31, the prime solution 35 is diverted through inner plasma port 32 by the supplied blood and an outer red blood cell layer 37 and an inner plasma layer 36 are formed (FIG. 5). Whole blood is continuously pumped by blood pump 22 into the separation chamber; plasma is continuously removed through the inner plasma port 32, and the red cells continuously leave the chamber via the outer erythrocyte port 33. The buffy-coat layer 38 accumulates between the red blood cell layer 37 and the plasma layer 36 (FIG. 5). The position of the buffy-coat is monitored by a monitoring device, which comprises the 8 hole imprint 34 and a camera (not shown).

FIG. 6 shows an advanced stage of the spillover of the buffy-coat from the separation chamber 30 via the inner plasma port 32 in direction to the spillover detector 115 (as indicated by the dashed arrow) and spillover clamp 110 of the automated blood cell separation device 1. Transfer of the buffy-coat is carried out by plasma pump 23.

Figure 7:
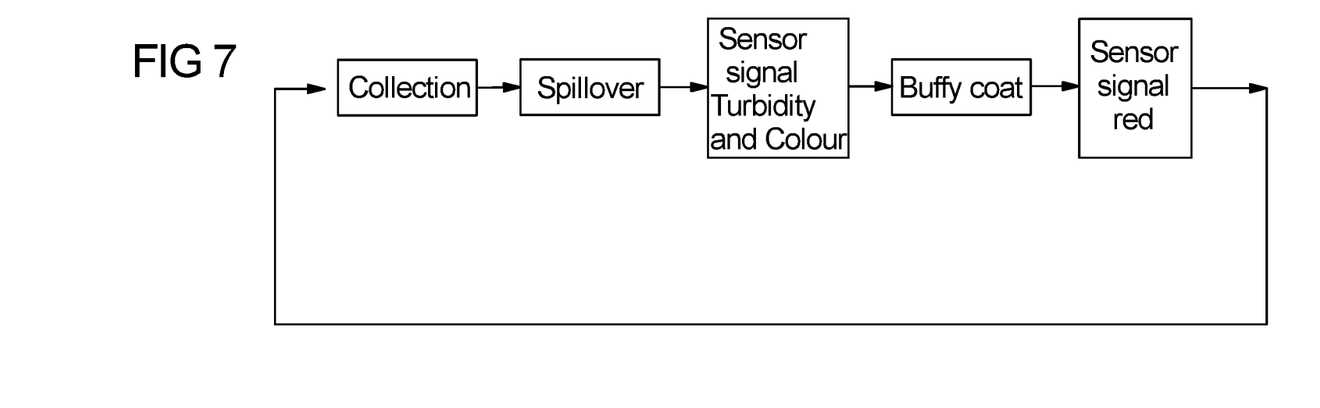
FIG. 7 shows schematically the cycle of the lymphocyte collection procedure.

FIG. 7 shows a cycle in the automated lymphocyte or stem cell collection procedure. "Collection" in the left-hand sided box means the separation and condensation of the red blood cell, plasma and buffy-coat fractions in the separation unit of the centrifuge compartment of the automated blood cell separation device of the invention. After the spillover phase is started, the turbidity of the fluid stream is monitored by the spillover detector 115. When the spillover detector detects an increase of the turbidity and, after passing of the white buffy coat comprising the platelets, an increase in the colour in the fluid stream, a signal is transmitted to a processor device 133, which in turn triggers the spillover clamp 110 to change its position into "collection" of the buffy-coat comprising lymphocytes and/or stem cells. The collection of the lymphocytes and/or stem cells is further monitored by the spillover detector. When the spillover detector detects a predefined threshold of the red colour in the fluid stream, a signal is transmitted to the processor device and the processor device triggers the spillover clamp to switch its position into "reinfusion", which terminates the collection of the lymphocytes and/or stem cells and the remainder of the unwanted blood fractions is reinfused into the donor/patient. If more lymphocytes and/or stem cells are to be collected, this cycle may be repeated several times.

The advantages of the method of the invention have been proven by separating and collecting stem cells from whole blood from donors/patients using the improved automated blood cell separation device 1 and the method of the invention. The haematocrit value of the stem cells collected was reduced compared to the volume driven spillover and buffy-coat phase: In particular, the hematocrit measured in the collected product (stem cells) was 3.8%. The same procedure was repeated with a second patient/donor and the hematocrit measured in the collected product (stem cells) in this case was 4.2%. Accordingly, the contamination of the stem cells collected with the blood cell separation device 1 and the method according to the invention with red blood cells has been decreased in comparison to Delfante et al., Journal of Clinical Apheresis, 21:227-232 (2006), where haematocrit values of 10.9% and 9.2% were achieved in stem cell fractions collected from patients and donors.

Figure 8:
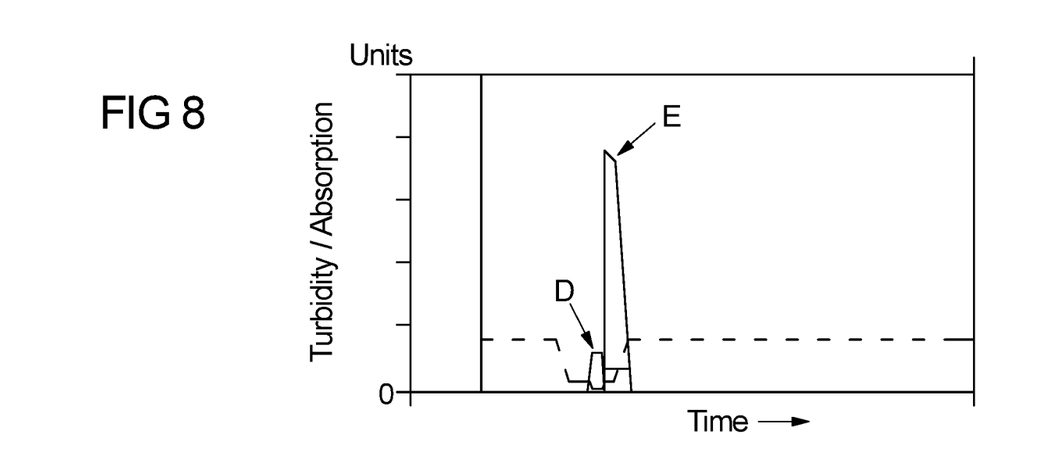
FIG. 8 shows signals resulting from monitoring the turbidity and the red colour of the fluid stream by the optical sensor comprised in the spillover detector.

FIG. 8 shows a flow chart visualizing the signals of the optical sensor comprised in the spillover detector used in the method of the invention. The spillover detector measures changes in the absorption caused by the plasma and/or cells comprised in the buffy-coat. The dashed line represents the blood flow during the lymphocyte collection. The black peaks represent the turbidity of the plasma (indicated by arrow D) and the red colour of the buffy-coat (indicated by arrow E).

Figure 9:
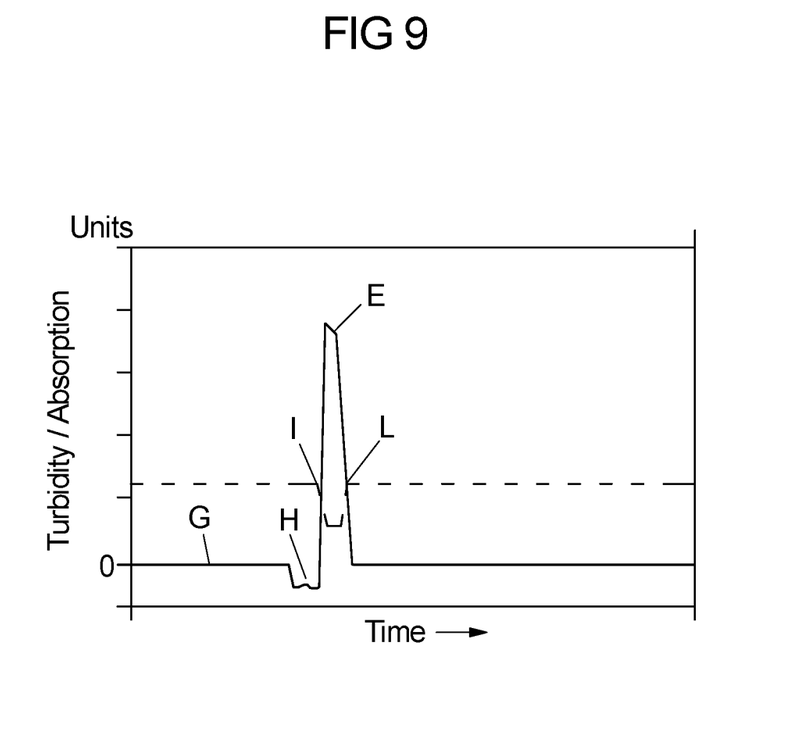
FIG. 9 shows signals resulting from monitoring the turbidity and colour of the fluid stream by the optical sensor comprised in the spillover detector, when targets cells, which have a reduced platelet count or are substantially free of platelets, shall be collected.

FIG. 9 shows a flow chart visualizing the signals of the optical sensor comprised in the spillover detector used in the method of the invention, when target cell fractions with reduced platelet count shall be collected. The spillover detector measures changes in the absorption caused by the plasma, platelets and target cells comprised in the buffy-coat. First, the sensor value is set to zero (G). A calibration is performed during every cycle. The colour signal drops, when white buffy coat, which contains the platelet fraction, is detected by the sensor (H). During the phases G and H, the spillover clamp 110 (see FIG. 3) is in position "reinfusion". An increase in the colour of the fluid stream indicates the end of the platelet fraction and the presence of the target cells in the fluid stream (I). Spillover clamp 110 (see FIG. 3) is now switched into the position "collect" and the target cells are transferred to and collected in the collection container 53. The spillover clamp 110 (see FIG. 3) is switched back into position "reinfusion" immediately after the spillover detector 115 has measured a red colour corresponding to the predefined threshold (L), and an additional volume of the target cells as described in FIG. 3 is collected.

LIST OF REFERENCE NUMERALS

1 Automated blood cell separation device, apheresis device
2 IV pole
3 Printer
4 Donor display
5 Wheels
10 Automatic valves/clamps
20 Pump section
21 ACD pump, plasma recirculation pump
22 Whole blood pump
23 Plasma pump
24 Cell pump
30 Separation chamber
31 blood port
32 Inner plasma port
33 Outer erythrocyte port
34 8 hole imprint
35 Saline
36 Plasma
37 Red blood cells
38 Buffy-coat
40 Centrifuge compartment, comprising a separation chamber 30

50 Collection/storage/stock bags and containers
51 Saline bag
52 Anti-coagulant bag
53, 54 Collection containers
55 Prime bag
56 Collection container
100 Front panel
101 Graphic user interface (GUI) with display and operating keys
102 "On"-button
103 "Off"-button
104 Pressure monitors
105 Return clamp
106 Saline inlet clamp
107 Saline outlet line clamp
108 Plasma collection clamp
109 Diversion clamp
110 Spillover clamp
111 ACD detector
112 Air detector
113 Plasma Hb/Hct detector
114 Replacement fluid detector
115 Spillover detector
116 Drip chamber
120 Blood tube
121 Inlet needle
122 Outlet tube to patient
123 Outlet needle
124 Plasma tube/buffy-coat tube
124' Buffy-coat tube
125 ACD tube
126, 126' Saline tubes
127 ACD pump
128 Connector of the pressure sensor—return pressure
129 Connector of the pressure sensor—inlet pressure
130 Connector to the transmembrane pressure sensor—P3
131 ACD drip chamber
132 Diversion tube
133 Processor device
134 Tube connecting the spillover detector 115 and the drip chamber 116o
F Fluid stream, filling direction
C Fluid stream, direction "collection"
R Fluid stream, direction "reinfusion"
D Turbidity peak
E Colour peak
G Zero value of colour
H Colour value of white buffy coat
I Colour value at the beginning of the target cell fraction
L Value of red colour corresponding to the predefined threshold (L)

The invention claimed is:

1. A method for separating lymphocytes and/or stem cells from whole blood in an automated blood cell separation device, comprising:
supplying blood to a separation chamber in a centrifugation unit of the automated blood cell separation device;
separating the blood in the separation chamber into red blood cell and plasma fractions, with a buffy-coat including lymphocytes and/or stem cells between the red blood cell and plasma fractions;
accumulating the buffy-coat between the red blood cell and plasma fractions in the separation chamber while portions of the red blood cell and plasma fractions are removed from the separation chamber, with said portion of the plasma fraction removed from the separation chamber flowing through a plasma/buffy-coat tube as part of a fluid stream;
causing a spillover in which the buffy-coat and then the red blood cell fraction exits the separation chamber and flows through the plasma/buffy-coat tube after said portion of the plasma fraction as parts of the fluid stream; and
transferring the buffy-coat from the plasma/buffy-coat tube into a collection container, wherein
a detector device of the automated blood cell separation device monitors at least turbidity and colour of the fluid stream in the plasma/buffy-coat tube,
the transfer of the buffy-coat into the collection container is automatically initiated when the detector device determines that the turbidity of the fluid stream in the plasma/buffy-coat tube has risen from a level indicating the presence of the plasma fraction to a level indicating the presence of the buffy-coat and that the colour of the fluid stream in the plasma/buffy-coat tube has changed from a colour indicating the presence of the plasma fraction to a colour indicating the presence of the buffy-coat, and
the transfer of the buffy-coat into the collection container is automatically terminated when the detector device determines that a predefined threshold of the colour of the fluid stream in the plasma/buffy-coat tube has been reached, with the predefined threshold of the colour of the fluid stream in the plasma/buffy-coat tube indicating the presence of the red blood cell fraction.

2. The method of claim 1, wherein the detector device comprises an optical sensor.

3. The method according to claim 2, wherein the optical sensor comprises a red LED for turbidity measurement and a green LED for measuring absorption of green light by the red blood cell fraction in the plasma/buffy-coat tube.

4. The method according to claim 3, further comprising monitoring at least a portion of the light emitted by the LEDs to enable compensation for aging effects and temperature drift in the LEDs.

5. The method according to claim 1, wherein
the detector device is configured to, upon detecting the increase of the turbidity and the change of the colour of the fluid stream in the plasma/buffy-coat tube, transmit a signal to a processor device, and
the processor device is configured to, upon receiving the signal from the detector device, initiate the transfer and collection of the buffy-coat by switching a position of a spillover clamp associated with the plasma/buffy-coat tube so as to direct the fluid stream in the plasma/buffy-coat tube into the collection container.

6. The method according to claim 1, wherein
the detector device is configured to, upon determining that the colour of the fluid stream in the plasma/buffy-coat tube has reached the predefined threshold, transmit a signal to a processor device, and
the processor device is configured to, upon receiving the signal from the detector device, terminate the transfer and collection of the buffy-coat by changing a position of a spillover clamp associated with the plasma/buffy-coat tube so as to direct the fluid stream in the plasma/buffy-coat tube away from the collection container.

7. The method according to claim 1, wherein the predefined threshold of the colour of the fluid stream in the plasma/buffy-coat tube corresponds to a red colour of a fluid having a hematocrit value of up to 5%.

8. A method for separating lymphocytes and/or stem cells from whole blood in an automated blood cell separation device, comprising:
supplying blood to a separation chamber in a centrifugation unit of the automated blood cell separation device;
separating the blood in the separation chamber into red blood cell and plasma fractions, with a buffy-coat including lymphocytes and/or stem cells between the red blood cell and plasma fractions;
accumulating the buffy-coat between the red blood cell and plasma fractions in the separation chamber while portions of the red blood cell and plasma fractions are removed from the separation chamber, with said portion of the plasma fraction removed from the separation chamber flowing through a plasma/buffy-coat tube as part of a fluid stream;
causing a spillover in which the buffy-coat and then the red blood cell fraction exits the separation chamber and flows through the plasma/buffy-coat tube after said portion of the plasma fraction as parts of the fluid stream; and
transferring the buffy-coat from the plasma/buffy-coat tube into a collection container, wherein
a detector device of the automated blood cell separation device monitors at least turbidity and colour of the fluid stream in the plasma/buffy-coat tube,
the transfer of the buffy-coat into the collection container is automatically initiated when the detector device determines that the turbidity of the fluid stream in the plasma/buffy-coat tube has risen from a level indicating the presence of the plasma fraction to a level indicating the presence of the buffy-coat and that the colour of the fluid stream in the plasma/buffy-coat tube has changed from a colour indicating the presence of the plasma fraction to a colour indicating the presence of the buffy-coat,
the transfer of the buffy-coat into the collection container is automatically terminated when the detector device determines that a predefined threshold of the colour of the fluid stream in the plasma/buffy-coat tube has been reached, with the predefined threshold of the colour of the fluid stream in the plasma/buffy-coat tube indicating the presence of the red blood cell fraction, and
the collection of the buffy-coat is terminated after detection of the predefined threshold of the colour of the fluid stream in the plasma/buffy-coat tube and after an additional default volume of the buffy-coat is allowed to pass a spillover clamp associated with the plasma/buffy-coat tube.

9. The method according to claim 8, wherein
said accumulating the buffy-coat in the separation chamber, said causing a spillover, and said transferring the buffy-coat are repeated in a plurality of cycles,
in at least one of the cycles, after detection of the predefined threshold of the colour of the fluid stream in the plasma/buffy-coat tube, said additional default volume of the buffy-coat is allowed to pass the spillover clamp before the collection of the buffy-coat for said at least one of the cycles is terminated, and
in at least one subsequent cycle, after detection of the predefined threshold of the colour of the fluid stream in the plasma/buffy-coat tube, said additional default volume of the buffy-coat allowed to pass the spillover clamp before the collection of the buffy-coat for said at least one subsequent cycle is terminated is reduced compared to the additional default volume of the buffy-coat allowed to pass the spillover clamp before the collection of the buffy-coat is terminated for said at least one of the cycles.

10. The method according to claim 1, wherein
the automated blood cell separation device is directly connected to a donor/patient and the blood, which is to be separated, is obtained via a needle from the donor/patient and supplied directly to the automated blood cell separation device, and
the plasma and red blood cell fractions are reinfused into the donor/patient via a second needle.

11. The method according to claim 1, wherein
the automated blood cell separation device is not connected to a patient,
said method is performed using blood samples that were already obtained from the patient, and
the plasma and red blood cell fractions are not reinfused into the patient but are collected in additional collection containers.

12. The method according to claim 1, wherein a product collected in the collection container substantially contains lymphocytes and/or stem cells.

13. The method according to claim 1, wherein a product collected in the collection container has a reduced count of platelets, granulocytes and red blood cells or is substantially free of platelets, granulocytes and red blood cells.

14. The method according to claim 13, wherein a product collected in the collection container has a hematocrit value, which is below 10% when stem cells are collected as the product, and below 5% when lymphocytes are collected as the product.

15. A blood cell separation device for separating lymphocytes and/or stem cells from whole blood in an automated procedure, comprising:
a pumping section for pumping a fluid through a tubing set including a plasma/buffy-coat tube installed on the blood cell separation device;
a centrifuge compartment, which comprises a separation chamber for the automated separation of buffy-coat from whole blood;
a detector device for determining the presence of target cells substantially containing lymphocytes and/or stem cells in a fluid stream in the plasma/buffy-coat tube, and for determining the presence of red blood cells in the fluid stream in the plasma/buffy-coat tube;
an automatic clamp for directing the fluid stream in the plasma/buffy-coat tube in a direction away from a collection container and for directing the fluid stream in the plasma/buffy-coat tube into the collection container; and
a processor device for controlling the automatic clamp, the processor device being constituted to switch the position of the automatic clamp to direct the fluid stream in the plasma/buffy-coat tube into the collection container when the detector device determines the target cells to be present in the plasma/buffy-coat tube, and the processor device being further constituted to switch the position of the automatic clamp to direct the fluid stream in the plasma/buffy-coat tube away from the collection container when the detector device determines the red blood cells to be present in the plasma/buffy-coat tube, wherein
the detector device monitors at least turbidity and colour of the fluid stream in the plasma/buffy-coat tube and the transfer of the target cells into the collection container is initiated when the detector device determines that the turbidity of the fluid stream in the plasma/buffy-coat tube has risen from a level indicating the absence of the target cells to a level indicating the presence of the target cells and that the colour of the fluid stream in the plasma/buffy-coat tube has changed from a colour indicating the absence of the target cells to a colour indicating the presence of the target cells, and the transfer of the target cells into the collection container is terminated when the detector device determines that a predefined threshold of the colour of the fluid stream in the plasma/buffy-coat tube has been reached, with the predefined threshold of the colour of the fluid stream in the plasma/buffy-coat tube indicating the presence of red blood cells.

16. The method according to claim 1, wherein said causing a spillover comprises increasing a rate at which the plasma fraction is removed from the separation chamber and reducing a rate at which whole blood is supplied to the separation chamber.

17. The method according to claim 1, wherein the predefined threshold of the colour of the fluid stream in the plasma/buffy-coat tube corresponds to a red colour of a fluid having a hematocrit value of up to 25%.

18. The method of claim 9, wherein
said additional default volume of the buffy-coat is allowed to pass the spillover clamp before the collection of the buffy-coat for the cycle is terminated for the first half of the cycles to be executed, and
said additional default volume of the buffy-coat allowed to pass the spillover clamp before the collection of the buffy-coat for the cycle is terminated is reduced for the second half of the cycles to be executed.

19. The method of claim 9, wherein the additional volume of the buffy-coat allowed to pass the spillover clamp before the collection of the buffy-coat for said at least one subsequent cycle is terminated is approximately half of the additional default volume of the buffy-coat allowed to pass the spillover clamp before the collection of the buffy-coat for said at least one of the cycles is terminated.

20. The method of claim 14, wherein the product collected in the collection container has a hematocrit value which is below 8% when stem cells are collected as a product and below 2% when lymphocytes are collected as the product.

* * * * *